United States Patent [19]

Greenfield et al.

[11] Patent Number: 5,356,562
[45] Date of Patent: Oct. 18, 1994

[54] FLUORO TOLANS AND LIQUID CRYSTALLINE MEDIA

[75] Inventors: Simon Greenfield, Creekmoor; Emma Brown, Dorset, both of Great Britain; Reinhard Hittich, Modautal, Fed. Rep. of Germany

[73] Assignee: Merck Patent Gesellschaft mit beschrankter Haftung, Darmstadt, Fed. Rep. of Germany

[21] Appl. No.: 852,258

[22] PCT Filed: Apr. 2, 1992

[86] PCT No.: PCT/EP92/00736
§ 371 Date: Jun. 3, 1992
§ 102(e) Date: Jun. 3, 1992

[87] PCT Pub. No.: WO92/18448
PCT Pub. Date: Oct. 29, 1992

[30] Foreign Application Priority Data

Apr. 13, 1991 [DE] Fed. Rep. of Germany ..... 91105897
Dec. 10, 1991 [DE] Fed. Rep. of Germany ..... 91121165

[51] Int. Cl.$^5$ ............ C09K 19/30; C09K 19/12; C07C 43/225; C07C 25/24
[52] U.S. Cl. ............ 252/299.63; 252/299.01; 252/299.66; 568/647; 568/655; 568/656; 570/127; 359/103
[58] Field of Search ............ 252/299.01, 299.63, 252/299.66; 359/103; 568/647, 655, 656; 570/127

[56] References Cited

U.S. PATENT DOCUMENTS 4,778,620 10/1988 Goto et al. ............ 252/299.63
5,164,114 11/1992 Kurmeier ............ 252/299.61
5,194,178 3/1993 Coates et al. ............ 252/299.63

FOREIGN PATENT DOCUMENTS 3206057 9/1991 Japan.

*Primary Examiner*—Shean Wu

[57] ABSTRACT

Fluoro tolans of the formula I

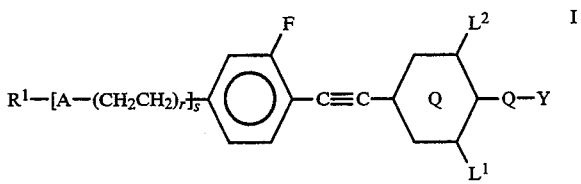

wherein
$R^1$ denotes alkyl with up to 12 carbon atoms wherein one or two non-adjacent $CH_2$ groups may also be replaced by —O—, —O—CO—, —CO—O— and/or —CH=CH—,
A is trans-1,4-cyclohexylene or 1,4-phenylene,
r is 0 or 1,
s is 0 or 1,
Q is —$CF_2$— or —$OCF_2$— and — if Y=F and/or $L^1$=$L^2$=F - also a single bond,
$L^1$ and $L^2$ are H or F, and
Y is H, F or Cl
are suitable as components of liquid crystalline media.

10 Claims, No Drawings

FLUORO TOLANS AND LIQUID CRYSTALLINE MEDIA

The invention relates to fluoro tolans of the formula I

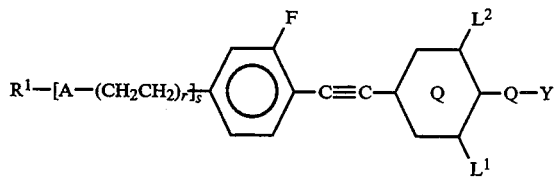

wherein $R^1$ denotes alkyl with up to 12 carbon atoms wherein one or two non-adjacent $CH_2$ groups may also be replaced by —O—, —O—CO—, —CO—O— and/or —CH=CH—, A is trans-1,4-cyclohexylene or 1,4-phenylene, r is 0 or 1, s is 0 or 1, Q is —$CF_2$— or —$OCF_2$— and — if Y=F and/or $L^1=L^2=F$ - also a single bond, $L^1$ and $L^2$ are H or F, and Y is H, F or Cl and also to liquid crystalline media being a mixture of at least 2 compounds characterized in that at least one compound is a fluoro tolane according to the formula I.

The compounds of the formula I can be used as components of liquid crystal media, in particular for displays which are based on the principle of the twisted nematic cell, including TN cells with a higher twist angle like STN, SBE, OMI etc., on the guest-host effect, on the effect of deformation of orientated phases or on the effect of dynamic scattering.

Similar halo tolans without lateral fluorine are described for example in GB 21 55 465.

Similar halo tolans are also disclosed in EP 02 76 067 and J6 26031. However, there are no examples in these application for compounds according to the invention.

Chloroalkoxy tolans are known from J. Malthete et al., Mol. Crys. Liq. Crys. 23, pp. 233 (1973). There is no hint at tolans as claimed in the present application.

The invention was based on the object of discovering new stable liquid crystal or mesogenic compounds which are suitable as components of liquid crystalline media and, in particular, have advantageous values for optical and dielectric anisotropy combined with low viscosity and high nematogenity.

It has now been found that the compounds of the formula I are highly suitable as polar components of liquid crystalline media. In particular, they have especially advantageous values of optical and dielectric anisotropy. It is also possible to obtain stable liquid crystal media with a broad nematic mesophase range including a good deep temperature behavior, a high resistivity and a comparatively low viscosity with the aid of these compounds.

By providing the compounds of the foumula I, the range of liquid crystal substances which are suitable under various technological aspects for the preparation of nematic mixtures is also quite generally widened considerably.

The compounds of the formula I can be used as base materials from which liquid crystal media are predominantly composed; however, they are preferably added to liquid crystal base materials of other classes of compounds, for example in order to influence the dielectric and/or optical anisotropy and/or the viscosity and/or the nematic mesophase range of such a dielectric.

The compounds of the formula I are colourless in the pure state and form liquid crystal mesophases in a temperature range which is favorably placed for electrooptical use. They are very stable towards chemicals, heat and light.

The invention thus relates to the compounds of the formula I and the use of these compounds as components of liquid crystal media. The invention furthermore relates to liquid crystal media with at least two liquid crystalline components, wherein at least one component is a compound of the formula I and to liquid crystal display elements, in particular electrooptical display elements, which contain media of this type.

Above and below $R^1$, A, r, s, Q, Y, $L^1$ and $L^2$ have the meaning given unless expressly stated otherwise.

The compounds of the formula I accordingly include the preferred tolans of the formula Ia to Ii, wherein Cyc is trans-1,4-cyclohexylene, Phe is 1,4-phenylene, PheF is

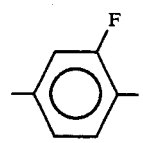

and PheFF

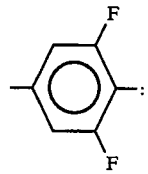

| | |
|---|---|
| $R^1$-PheF-C≡C-Ph-Q-Y | Ia |
| $R^1$-PheF-C≡C-PheF-Q-Y | Ib |
| $R^1$-PheF-C≡C-PheFF-Q-Y | Ic |
| $R^1$-Cyc-PheF-C≡C-Ph-Q-Y | Id |
| $R^1$-Cyc-PheF-C≡C-PheF-Q-Y | Ie |
| $R^1$-Cyc-PheF-C≡C-PheFF-Q-Y | If |
| $R^1$-Cyc-$CH_2CH_2$-PheF-C≡C-Ph-Q-Y | Ig |
| $R^1$-Cyc-$CH_2CH_2$-PheF-C≡C-PheF-Q-Y | Ih |
| $R^1$-Cyc-$CH_2CH_2$-PheF-C≡C-PheFF-Q-Y | Ii |

$R^1$ is preferably alkyl, alkoxy, oxaalkyl or alkenyl and can exhibit a straight-chain or branched structure. Especially preferred are compounds of subformula Ig (Q-Y is preferably $OCF_3$, $OCHF_2$ or Cl) and of subformula Ih (Q-Y is preferably $OCF_3$, $OCHF_2$, F or Cl).

Alkyl or alkoxy preferably are straight-chain and have 2, 3, 4, 5, 6 or 7 C atoms. Accordingly they are preferably ethyl, propyl, butyl, pentyl, hexyl, heptyl, ethoxy, propoxy, butoxy, pentoxy, hexoxy or heptoxy, also methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxybutyl (=2-methoxyethyl), 2-, 3- or 4-oxapentyl, 2-, 3-, 4- or 5-oxahexyl, 2-, 3-, 4-5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8-, or 9-oxadecyl.

Alkenyl is preferably straight-chain and has 2 or 10 C atoms. It is accordingly, in particular, vinyl, prop-1- or prop-2-enyl, but-1-, -2- or -3-enyl, pent-1-, -2-, -3-or -4-enyl, hex-1-, -2-, -3-, -4- or -5-enyl, hept-1-, -2-, -3-, -4-, -5-or -6-enyl, oct-1-, -2-, -3-, -4-, -5- -6- or -7-enyl, non-1-, -2-, -3-, -4-, -5-, -6-, -7-or -8-enyl or dec-1-, -2-, -3-, -4-, -5-, -6-, -7-, -8- or -9-enyl.

Compounds of the formula I containing a branched terminal group can occasionally be of importance because of an improved solubility in the customary liquid crystal base materials, but in particular as chiral doping substances if they are optically active. Branched groups of this type as a rule contain not more than one chain branching. Preferred branched radicals are isopropyl, 2-butyl (=1-methylpropyl), isobutyl (=2-methylpropyl, 2-methylbutyl, isopentyl, (=3-methylbutyl), 2-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 2-methylhexoxy, 1-methylhexoxy, 1-methylheptoxy (=2-octyloxy), 2-oxa-3-methylbutyl, 3-oxa-4-methylpentyl, 4-methylhexyl, 2-nonyl, 2-decyl, 2-dodecyl, 6-methyloctoxy, oxy, 2-methyl-3-oxapentyl and 2-methyl-3-oxahexyl.

In the case of compounds with a branched terminal group $R^1$, formula I includes both the optical antipodes and racemates as well as mixtures thereof.

A is preferably trans-1,4-cyclohexylene. $L^1$ is preferably H and $L^2$ is preferably F. Also preferred are tolans wherein $L^1$ and $L^2$ denote F. If Q-Y=F or if Q=CF$_2$ or OCF$_2$ also those tolans are preferred wherein $L^1$ and $L^2$ are hydrogen.

Of the compounds of the formula I and subformulae thereof, those in which at least one of the radicals contained therein has one of the preferred meanings given are preferred.

The compounds of the formula I are prepared by methods which are known per se, such as are described in the literature (for example in the standard works, such as Houben-Weyl, Methoden der Organischen Chemie Methods of Organic Chemistry, Georg Thieme Verlag, Stuttgart), and in particular under reaction conditions which are known and suitable for the reactions mentioned. Variants which are known per se and are not mentioned in more detail here can also be used in this connection.

If desired, the starting materials can also be formed in situ, such that they are not isolated from the reaction mixture but are immediately reacted further to give the compounds of the formula I.

The compounds of the formula I can thus be prepared by brominating the corresponding stilbenes and subsequently subjecting them to a dehydrohalogenation. Variants of this reaction which can be used are known per se and are not mentioned in detail here.

The stilbenes can be prepared by reacting a 4-substituted benzaldehyde with a corresponding phosphorous ylide according to Wittig or by reacting a 4-substituted phenylethylene with a corresponding bromobenzene derivative according to Heck. A further possibility of forming the C≡C triple bond consists in reacting a compound which corresponds to the formula I except that it contains a —CH$_2$—CO— group in place of the —C≡C-bond, either with an inorganic acid chloride and dehydrohalogenating the —CH$_2$—CCl$_2$— group then formed in the presence of a base, or reacting the compound with semicarbazide and selenium dioxide and subsequently converting it into the triple bond by heating in the presence of methyllithium.

It is also possible to convert a corresponding benzil derivative into the tolane using hydrazine and subsequently HgO.

Compounds of the formula I can also be prepared by coupling alkynyl-zinc compounds with arylhalides analogously to the process described by A. O. King, E. Negishi, F. J. Villani and A. Silveira in J. Org. Chem. 43 (1978) 358.

Compounds of the formula I can also be prepared by the Fritsch-Buttenberg-Wiechell rearrangement (Ann. 279, 319, 327, 332, 1894) in which 1,1-diaryl-2-halogenoethylenes are rearranged in the presence of strong bases to form diarylacetylenes.

Preferably, compounds of the formula I are prepared from 4-substituted phenylacetylenes and aryl halides in the presence of a palladium catalyst, for example bis-(triphenylphosphine)-palladium(II) chloride and copper(I) iodide (described in Synthesis (1980) 627 or Tetrahedron Letters 27 (1986) 1171).

Other routes are apparent to the skilled worker. All these steps and the corresponding reaction conditions are known to the skilled worker.

In addition to one or more compounds for formula I the liquid crystal media according to the invention preferably contain 2-40 components and in particular 4-30 components. Liquid crystal media being composed of one or more compounds of formula I and 7-25 other components are especially preferred.

These additional components are preferably chosen from the nematic or nematogenic (monotropic or isotropic) substances; in particular from the classes of azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenylbenzoates, cyclohexylphenyl cyclohexanecarboxylates, cyclohexylphenyl cyclohexylcyclohexanecarboxylates, phenylcyclohexanes, cyclohexylbiphenyls, phenylcyclohexylcyclohexanes, cyclohexylcyclohexanes, cyclohexylcyclohexenes, cyclohexylcyclohexylcyclohexene, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl-or cyclohexyl-1,3-dithianes, 1,2-diphenylethanes, 1,2-dicyclohexylethanes, 1-phenyl-2-cyclohexylethanes, 1-cyclohexyl-2-(4-phenyl-cyclohexyl)-ethanes, 1-cyclohexyl-2-biphenylethanes, 1-phenyl-2-cyclohexyl-phenylethanes, optionally halogenated stilbenes, benzyl phenyl ethers, tolans and substituted cinnamic acids.

The 1,4-phenylene groups of these compounds may be fluorinated.

The most important compounds which are possible constituents of liquid crystal media according to the invention can be characterized by the formalae 1, 2, 3, 4 and 5:

R'-L-U-R"    1

R'-L-COO-U-R"    2

R'-L-OOC-U-R"    3

R'-L-CH$_2$CH$_2$-U-R"    4

R'-L-C≡C-U-R"    5

In the formulae 1, 2, 3, 4 and 5 L and U may be equal or different from each other. L and U independently from each other denote a bivalent residue selected from the group consisting of —Phe—, —Cyc—, —Phe—Phe—, —Phe—Cyc—, —Cyc—Cyc—, —Pyr—, —Dio—, —G—Phe—, —G—Cyc— and their mirror images; in this compilation of residues Phe denotes unsubstituted or fluorinated 1,4-phenylen, Cyc trans- 1,4-cyclohexylene or 1,4-cyclohexenylen, Pyr pyrimidine-2,5-diyl or pyridine-2,5-diyl, Dio 1,3-dioxane-2,5-diyl and G 2-(trans-1,4-cyclohexyl)-ethyl, pyrimidine-2,5-diyl, pyridine-2,5-diyl or 1,3-dioxane-2,5-diyl.

One of the residues L and U is preferably Cyc, Phe or Pyr. U preferably denotes Cyc, Phe or Phe-Cyc. The liquid crystal media according to the invention preferably contain one or more components selected from the compounds of formulae 1, 2, 3, 4 and 5 with L and U meaning Cyc, Phe and Pyr, said liquid crystal media further containing at the same time one or more components selected from the compounds of formulae 1, 2, 3, 4 and 5 with one of the residues L and U denoting Cyc, Phe and Pyr and the other residue being selected from the group consisting of —Phe—Phe—, —Phe—Cyc—, —Cyc—Cyc—, —G—Cyc—, said liquid crystal media containing in addition to this optionally one or more components selected from the compounds of formulae 1, 2, 3, 4 and 5 with L and U being selected from the group consisting of —Phe—Cyc—, —Cyc—Cyc—, —G—Phe— and —G—Cyc.

In a preferred subgroup of the compounds of formulae 1, 2, 3, 4 and 5 (subgroup 1) R' and R" are independently from each other alkyl, alkenyl, alkoxy, alkenoxy with up to 8 carbon atoms. R' and R" differ from one another in most of these compounds, one of the residues usually being alkyl or alkenyl. In another preferred subgroup of the compounds of formulae 1, 2, 3, 4 and 5 (subgroup 2) R" denotes —CN, —CF$_3$, —OCF$_3$, —OCHF$_2$, —F, —Cl or —NCS while R' has the meaning indicated in subgroup 1 and is preferably alkyl or alkenyl. Other variants of the envisaged substituents in the compounds of formulae 1, 2, 3, 4 and 5 are also customary. Many such substances are commercially available. All these substances are obtainable by methods which are known from the literature or by analogous methods.

The liquid crystal media according to the invention preferably contain in addition to components selected from subgroup 1 also components of subgroup 2, the percentage of these components being as follows:

subgroup 1:20 to 90%, in particular 30 to 90%
subgroup 2:10 to 50%, in particular 10 to 50%

In these liquid crystal media the percentages of the compounds according to the invention and the compounds of subgroup 1 and 2 may add up to give 100%.

The media according to the invention preferably contain 1 to 40%, in particular 5 to 30% of the compounds according to the invention. Media containing more than 40%, in particular 45 to 90% of the compounds according to the invention are further preferred. The media contain preferably 3, 4 or 5 compounds according to the invention. The media according to the invention are prepared in a manner which is customary per se. As a rule, the components are dissolved in one another, advantageously at elevated temperature. The liquid crystal media according to the invention can be modified by suitable additives so that they can be used in all the types of liquid crystal display devices. Such additives are known to the expert and are described in detail in the literature (H. Kelker/R. Hatz, Handbook of Liquid Crystals, Verlag Chemie, Weinheim, 1980). For example, it is possible to add pleochroic dyestuffs to prepare colored guest-host systems or substances for modifying the dielectric anisotropy, the viscosity and/or the orientation of the nematic phases.

The following examples are to be construed as merely illustrative and not limitative. m.p.=melting point, c.p.=clearing point. In the foregoing and in the following all parts and percentages are by weight and the temperatures are set forth in degrees Celsius. "Customary work-up" means that water is added, the mixture is extracted with methylene chloride, the organic phase is separated off, dried and evaporated, and the product is purified by crystallization and/or chromatography.

Further are:

C: crystalline-solid state, S: smectic phase (the index denoting the typ of smectic phase), N: nematic phase, Ch: cholesteric phase, I: isotropic phase. The number being embraced by 2 of these symbols denotes the temperature of phase change.

EXAMPLE 1 a) A mixture of 0.1 mol of 4-pentyl-2-fluoro-iodobenzene, 0.12 mol of trimethylsilylacetylene, 0.0014 mol of bis(triphenylphosphine)-palladium(II) chloride Pd(PPh$_3$)$_2$Cl$_2$ and 0.7 mmol of copper (I) iodide in 250 ml diethylamine is stirred at room temperature for 20 hours. After evaporation of the solvent the crude product is purified by chromatography on alumina (4:1 petrol/difluoromethane) to give 2-(4-pentylphenyl)-1-trimethylsilylacetylene. Removal of the trimethylsilylgroup is accomplished by treatment this acetylene in methanol with 1M KOH for 1 hour at room temperature. Evaporation of the methanol and either extraction yields 4-pentyl-2-fluoro-phenylacetylene.

b) 0.2 mmol of Pd(PPh$_3$)$_2$Cl$_2$ and 0.1 mmol of CuI are added to a mixture of 0.01 mol of 4-pentylphenylacetylene, 0.01 mol of 3,4-difluoro-iodobenzene and 40 ml of diethylamine at room temperature and stirred for 12 hours. After completion of the reaction, the suspension is filtered, and the filtrate is concentrated by evaporation. Purification by chromatography and/or crystallization gives 4-pentyl-2-fluoro-3',4'-difluoro tolan.

The following are prepared analogously ($R^1$=straight-chained alkyl with n carbon atoms):

| n | A | r | s | L1 | L2 | Q | Y |
|---|---|---|---|----|----|----|----|
| 3 | — | 0 | 0 | H | H | OCF$_2$ | H |
| 3 | — | 0 | 0 | H | H | OCF$_2$ | F |
| 3 | — | 0 | 0 | H | F | OCF$_2$ | Cl |
| 3 | — | 0 | 0 | H | F | — | Cl |
| 3 | — | 0 | 0 | F | F | — | Cl |
| 3 | — | 0 | 0 | F | F | — | F |
| 3 | — | 0 | 0 | F | H | — | F |
| 3 | — | 0 | 0 | H | H | — | F |

| n | A | r | s | L1 | L2 | Q | Y |
|---|---|---|---|----|----|---|---|
| 5 | — | 0 | 0 | H | H | $OCF_2$ | H |
| 5 | — | 0 | 0 | H | H | $OCF_2$ | F, C 9 I ($S_A$ —17N —8I) |
| 5 | — | 0 | 0 | H | F | $OCF_2$ | Cl |
| 5 | — | 0 | 0 | H | F | — | Cl |
| 5 | — | 0 | 0 | F | F | — | Cl |
| 5 | — | 0 | 0 | F | F | — | F |
| 5 | — | 0 | 0 | F | H | — | F |
| 5 | — | 0 | 0 | H | H | — | F, C 17 I (N —20I) |
| 3 | Cyc | 0 | 1 | H | H | $OCF_2$ | H |
| 3 | Cyc | 0 | 1 | H | H | $OCF_2$ | F |
| 3 | Cyc | 0 | 1 | H | F | $OCF_2$ | Cl |
| 3 | Cyc | 0 | 1 | H | F | — | Cl |
| 3 | Cyc | 0 | 1 | F | F | — | Cl |
| 3 | Cyc | 0 | 1 | F | F | — | F |
| 3 | Cyc | 0 | 1 | F | H | — | F |
| 3 | Cyc | 0 | 1 | H | H | — | F |
| 3 | Cyc | 1 | 1 | H | H | $OCF_2$ | H |
| 3 | Cyc | 1 | 1 | H | H | $OCF_2$ | F |
| 3 | Cyc | 1 | 1 | H | F | $OCF_2$ | Cl |
| 3 | Cyc | 1 | 1 | H | F | — | Cl |
| 3 | Cyc | 1 | 1 | F | F | — | Cl |
| 3 | Cyc | 1 | 1 | F | F | — | F |
| 3 | Cyc | 1 | 1 | F | H | — | F |
| 3 | Cyc | 1 | 1 | H | H | — | F, C 5 1.1 N 130.9 I |
| 2 | Cyc | 0 | 1 | H | H | $OCF_2$ | H |
| 2 | Cyc | 0 | 1 | H | H | $OCF_2$ | F |
| 2 | Cyc | 0 | 1 | H | F | $OCF_2$ | Cl |
| 2 | Cyc | 0 | 1 | H | F | — | Cl |
| 2 | Cyc | 0 | 1 | F | F | — | Cl |
| 2 | Cyc | 0 | 1 | F | F | — | F |
| 2 | Cyc | 0 | 1 | F | H | — | F |
| 2 | Cyc | 0 | 1 | H | H | — | F |
| 2 | Cyc | 1 | 1 | H | H | $OCF_2$ | H |
| 2 | Cyc | 1 | 1 | H | H | $OCF_2$ | F |
| 2 | Cyc | 1 | 1 | H | F | $OCF_2$ | Cl |
| 2 | Cyc | 1 | 1 | H | F | — | Cl |
| 2 | Cyc | 1 | 1 | F | F | — | Cl |
| 2 | Cyc | 1 | 1 | F | F | — | F |
| 2 | Cyc | 1 | 1 | F | H | — | F |
| 2 | Cyc | 1 | 1 | H | H | — | F |
| 4 | Cyc | 0 | 1 | H | H | $OCF_2$ | H |
| 4 | Cyc | 0 | 1 | H | H | $OCF_2$ | F |
| 4 | Cyc | 0 | 1 | H | F | $OCF_2$ | Cl |
| 4 | Cyc | 0 | 1 | H | F | — | Cl |
| 4 | Cyc | 0 | 1 | F | F | — | Cl |
| 4 | Cyc | 0 | 1 | F | F | — | F |
| 4 | Cyc | 0 | 1 | F | H | — | F |
| 4 | Cyc | 0 | 1 | H | H | — | F |
| 4 | Cyc | 1 | 1 | H | H | $OCF_2$ | H |
| 4 | Cyc | 1 | 1 | H | H | $OCF_2$ | F |
| 4 | Cyc | 1 | 1 | H | F | $OCF_2$ | Cl |
| 4 | Cyc | 1 | 1 | H | F | — | Cl |
| 4 | Cyc | 1 | 1 | F | F | — | Cl |
| 4 | Cyc | 1 | 1 | F | F | — | F |
| 4 | Cyc | 1 | 1 | F | H | — | F |
| 4 | Cyc | 1 | 1 | H | H | — | F |
| 5 | Cyc | 0 | 1 | H | H | $OCF_2$ | H |
| 5 | Cyc | 0 | 1 | H | H | $OCF_2$ | F |
| 5 | Cyc | 0 | 1 | H | F | $OCF_2$ | Cl |
| 5 | Cyc | 0 | 1 | H | F | — | Cl |
| 5 | Cyc | 0 | 1 | F | F | — | Cl |
| 5 | Cyc | 0 | 1 | F | F | — | F |
| 5 | Cyc | 0 | 1 | F | H | — | F |
| 5 | Cyc | 0 | 1 | H | H | — | F, C 78.4 N 162.9 I |
| 5 | Cyc | 1 | 1 | H | H | $OCF_2$ | H |
| 5 | Cyc | 1 | 1 | H | H | $OCF_2$ | F |
| 5 | Cyc | 1 | 1 | H | F | $OCF_2$ | Cl |
| 5 | Cyc | 1 | 1 | H | F | — | Cl |
| 5 | Cyc | 1 | 1 | F | F | — | Cl |
| 5 | Cyc | 1 | 1 | F | F | — | F |
| 5 | Cyc | 1 | 1 | F | H | — | F |
| 5 | Cyc | 1 | 1 | H | H | — | F |
| 3 | Phe | 0 | 1 | H | H | $OCF_2$ | H |
| 3 | Phe | 0 | 1 | H | H | $OCF_2$ | F |
| 3 | Phe | 0 | 1 | H | F | $OCF_2$ | Cl |
| 3 | Phe | 0 | 1 | H | F | — | Cl |
| 3 | Phe | 0 | 1 | F | F | — | Cl |
| 3 | Phe | 0 | 1 | F | F | — | F |
| 3 | Phe | 0 | 1 | F | H | — | F |
| 3 | Phe | 1 | 1 | H | H | $OCF_2$ | H |
| 3 | Phe | 1 | 1 | H | H | $OCF_2$ | F |
| 3 | Phe | 1 | 1 | H | F | $OCF_2$ | Cl |
| 3 | Phe | 1 | 1 | H | F | — | Cl |
| 3 | Phe | 1 | 1 | F | F | — | Cl |
| 3 | Phe | 1 | 1 | F | F | — | F |
| 3 | Phe | 1 | 1 | F | H | — | F |
| 3 | Phe | 1 | 1 | H | H | — | F |
| 2 | Phe | 0 | 1 | H | H | $OCF_2$ | H |
| 2 | Phe | 0 | 1 | H | H | $OCF_2$ | F |
| 2 | Phe | 0 | 1 | H | F | $OCF_2$ | Cl |
| 2 | Phe | 0 | 1 | H | F | — | Cl |
| 2 | Phe | 0 | 1 | F | F | — | Cl |
| 2 | Phe | 0 | 1 | F | F | — | F |
| 2 | Phe | 0 | 1 | F | H | — | F |
| 2 | Phe | 0 | 1 | H | H | — | F |
| 2 | Phe | 1 | 1 | H | H | $OCF_2$ | H |
| 2 | Phe | 1 | 1 | H | H | $OCF_2$ | F |
| 2 | Phe | 1 | 1 | H | F | $OCF_2$ | Cl |
| 2 | Phe | 1 | 1 | H | F | — | Cl |
| 2 | Phe | 1 | 1 | F | F | — | Cl |
| 2 | Phe | 1 | 1 | F | F | — | F |
| 2 | Phe | 1 | 1 | F | H | — | F |
| 2 | Phe | 1 | 1 | H | H | — | F |
| 4 | Phe | 0 | 1 | H | H | $OCF_2$ | H |
| 4 | Phe | 0 | 1 | H | H | $OCF_2$ | F |
| 4 | Phe | 0 | 1 | H | F | $OCF_2$ | Cl |
| 4 | Phe | 0 | 1 | H | F | — | Cl |
| 4 | Phe | 0 | 1 | F | F | — | Cl |
| 4 | Phe | 0 | 1 | F | F | — | F |
| 4 | Phe | 0 | 1 | F | H | — | F |
| 4 | Phe | 0 | 1 | H | H | — | F |
| 4 | Phe | 1 | 1 | H | H | $OCF_2$ | H |
| 4 | Phe | 1 | 1 | H | H | $OCF_2$ | F |
| 4 | Phe | 1 | 1 | H | F | $OCF_2$ | Cl |
| 4 | Phe | 1 | 1 | H | F | — | Cl |
| 4 | Phe | 1 | 1 | F | F | — | Cl |
| 4 | Phe | 1 | 1 | F | F | — | F |
| 4 | Phe | 1 | 1 | F | H | — | F |
| 4 | Phe | 1 | 1 | H | H | — | F |
| 5 | Phe | 0 | 1 | H | H | $OCF_2$ | H |
| 5 | Phe | 0 | 1 | H | H | $OCF_2$ | F |
| 5 | Phe | 0 | 1 | H | F | $OCF_2$ | Cl |
| 5 | Phe | 0 | 1 | H | F | — | Cl |
| 5 | Phe | 0 | 1 | F | F | — | Cl |
| 5 | Phe | 0 | 1 | F | F | — | F |
| 5 | Phe | 0 | 1 | F | H | — | F |
| 5 | Phe | 0 | 1 | H | H | — | F |
| 5 | Phe | 1 | 1 | H | H | $OCF_2$ | H |
| 5 | Phe | 1 | 1 | H | H | $OCF_2$ | F |
| 5 | Phe | 1 | 1 | H | F | $OCF_2$ | Cl |
| 5 | Phe | 1 | 1 | H | F | — | Cl |
| 5 | Phe | 1 | 1 | F | F | — | Cl |
| 5 | Phe | 1 | 1 | F | F | — | F |
| 5 | Phe | 1 | 1 | F | H | — | F |
| 5 | Phe | 1 | 1 | H | H | — | F |

(— = single bond)

EXAMPLE 2

The liquid crystalline media A and B which are composed as follows:

| Composition (weight %) | A | B |
|---|---|---|
|  $C_3H_7$—H—$CH_2CH_2$—⌬—CN | 10.0 | 10.0 |
|  $C_3H_7$—H—⌬—CN | 24.0 | 24.0 |
|  $C_5H_{11}$—H—⌬—CN | 5.0 | 5.0 |

-continued

| | A | B |
|---|---|---|
| C3H7—[H]—[O]—OC2H5 | 19.0 | 16.0 |
| C3H7—[H]—[H]—CH2CH2—[O]—CH3 | 6.0 | 6.0 |
| C3H7—[H]—[H]—CH2CH2—[O]—C2H5 | 6.0 | 5.0 |
| C3H7—[H]—[H]—CH2CH2—[O]—C3H7 | 5.0 | 5.0 |
| C3H7—[H]—[O]—[O]—C2H5 | 6.0 | 6.0 |
| C5H11—[H]—[O]—[O]—C2H5 | 6.0 | 6.0 |
| CH3—[O]—C≡C—[O]—OC2H5 | 4.0 | — |
| C2H5—[O]—C≡C—[O]—OCH3 | 4.0 | 6.0 |
| C3H7—[H]—[H]—[O]—OCF3 | — | 5.0 |
| C3H7—[H]—CH2CH2—[O(F)]—C≡C—[O]—F | 5.0 | 6.0 | show the following parameters:

| | A | B |
|---|---|---|
| S—N [°C] | <−40 | <−40 |
| Clearing point [°C] | 73 | 77 |
| Viscosity at 20° C. [mm²s⁻¹] | 16 | 16 |
| Δn (589 nm, 20° C.) | 0.1364 | 0.1330 |

EXAMPLE 3

A supertwisted liquid crystal device (240° twist, yellow mode, 1:200 duty, 1:15 bias, 128 Hz) based on the mixtures A and B of example 2 and a commercially available dopant S-811 (E. Merck, Darmstadt) is made and tested as follows:

| | A | B |
|---|---|---|
| $V_{10}$ (Volt) | 2.34 | 2.35 |
| $V_{90}$ (Volt) | 2.44 | 2.45 |
| $V_{90}/V_{10}$ | 1.043 | 1.043 |
| $(T_{on} + T_{off})/2$ (msec) | 201 | 201 |

We claim:
1. Fluoro tolans of the formula I

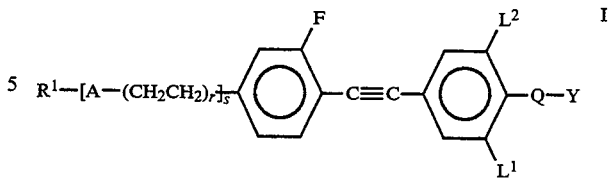

wherein
$R^1$ denotes alkyl with up to 12 carbon atoms wherein one or two non-adjacent $CH_2$ groups may also be replaced by —O—, —O—CO—, —CO—O— and/or —CH=CH—,
A is trans-1,4-cyclohexylene or 1,4-phenylene,
r is 0 or 1,
s is 0 or 1,
Q is —$CF_2$—, —$OCF_2$— or a single bond,
$L^1$ is H,
$L^2$ is H or F, and
Y is F.

2. Fluoro tolans of claim 1, wherein $L^1$ is H and $L^2$ is F.

3. Fluoro tolans of claim 1, wherein $L^1 = L^2 = H$, Q=—$OCF_2$ and $R^1$ is alkyl having 2 to 12 carbon atoms.

4. Fluoro tolans of claim 1, wherein s is 0 and $R^1$ is an alkyl group with up to 10 carbon atoms.

5. Fluoro tolans of claim 1, wherein s is 1, r is 0 and A is trans-1,4-cyclohexylene.

6. Fluoro tolans of claim 1, wherein s and r are 1 and A is trans-1,4-cyclohexylene.

7. Liquid crystalline medium being a mixture of at least two compounds, characterized in that at least one compound is a fluoro tolan according to claim 1.

8. Liquid crystal display device, characterized in that it contains a liquid crystalline medium according to claim 7.

9. Electrooptical display device, characterized in that it contains a liquid crystalline medium according to claim 7.

10. Fluoro tolans of the formula I

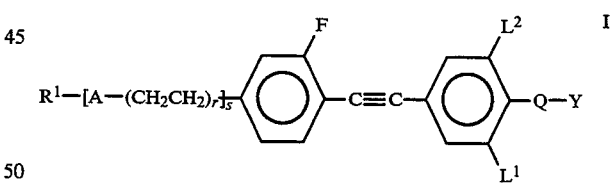

wherein
$R^1$ denotes alkyl with up to 12 carbon atoms wherein one or two non-adjacent $CH_2$ groups may also be replaced by —O—, —O—CO—, —CO—O— and/or —CH=CH—,
A is trans-1,4-cyclohexylene or 1,4-phenylene,
r is 0 or 1,
s is 0 or 1,
Q is —$CF_2$—, —$OCF_2$— or a single bond,
$L^1$ is H,
$L^2$ is H, and
Y is F.

* * * * *